United States Patent [19]

Labowsky et al.

[11] Patent Number: 4,531,056
[45] Date of Patent: Jul. 23, 1985

[54] METHOD AND APPARATUS FOR THE MASS SPECTROMETRIC ANALYSIS OF SOLUTIONS

[75] Inventors: Michael J. Labowsky, Wayne, N.J.; John B. Fenn, Branford, Conn.; Masamichi Yamashita, Tokyo, Japan

[73] Assignee: Yale University, New Haven, Conn.

[21] Appl. No.: 486,645

[22] Filed: Apr. 20, 1983

[51] Int. Cl.³ .............................................. B01D 59/44
[52] U.S. Cl. ................................... 250/288; 250/281; 250/282; 250/286
[58] Field of Search ................. 250/281, 282, 288, 286

[56] References Cited

U.S. PATENT DOCUMENTS 4,121,099 10/1978 French et al. ........................ 250/296
4,209,696 6/1980 Fite .
4,300,044 11/1981 Iribarne et al. .

OTHER PUBLICATIONS

*Analytical Chemistry,* 1979, vol. 51, pp. 682A–701A, Arpino, P. J. and Guichon, G.
"1st Workshop on LC/MS," Published in *Journal of Chromatography,* 1982, vol. 251, pp. 91–225, (Montreux, Oct. 1981).
*Journal of Electrostatics,* 1978, vol. 5, p. 411, Stimson, B. A. and Evans, C. A., Jr.
*Biopolymers,* 1971, vol. 10, pp. 821–826–Clegg, G. A. and Dole, M.
Adv. in Chem., (1973), vol. 125, p. 73–Dole, M., Cox, H. L., Jr., Gleniec, J.
*The Journal of Physical Chemistry,* vol. 82, No. 6, (1978), p. 660, Stimpson, B. A. and Evans, C. A., Jr.
*Journal of Chemical Physics,* (1968), vol. 49, No. 5, pp. 2240–2249, Dole, M., Mack, L. L., Hines, R. L., Mobley, R. C., Ferguson, L. D.
*The Journal of Chemical Physics,* vol. 52, (10), 1970, 4977–4986.

Primary Examiner—Bruce C. Anderson
Assistant Examiner—Paul A. Guss
Attorney, Agent, or Firm—Birch, Stewart, Kolasch & Birch

[57] ABSTRACT

An electrospray ion source for a mass spectrometer capable of generating ions from samples dissolved in a solution comprises a capillary tube through which the said solution is pumped into a first chamber maintained substantially at atmospheric pressure and in which an inert gas is flowing in a direction counter to the flow of the solution, and a small orifice in the end wall of the chamber opposite to and aligned with the capillary. A high potential difference is applied between the capillary and the end wall so that the solution is electrosprayed into the chamber and ions characteristic of the sample are formed. These ions are desolvated to a controllable extent by the inert gas, which may also be heated to improve the efficiency of the process and increase the maximum permissible flow rate of solution. The ions so formed pass through the small orifice into a second chamber maintained at a reduced pressure, and into a mass spectrometer. Alternatively an additional pressure reduction stage can be included, so that the ions pass into a third chamber maintained at a still lower pressure in which the mass spectrometer is situated through a conventional nozzle and skimmer arrangement. The ion source is particularly effective for the production of unfragmented and unsolvated ions from thermally unstable or involatile samples, and may be used as a liquid chromatograph—mass spectrometer interface.

37 Claims, 5 Drawing Figures

METHOD AND APPARATUS FOR THE MASS SPECTROMETRIC ANALYSIS OF SOLUTIONS

TECHNICAL FIELD

This invention relates to a method for the mass spectrometric analysis of chemical compounds in solution, especially when the solution is the effluent of a liquid chromatograph, which is particularly suitable for compounds which are either thermally unstable or involatile.

BACKGROUND ART

The direct mass spectrometric analysis of solutions, especially those in which the solutes are thermally unstable or involatile, has long presented difficulties. There have been a number of different approaches, as reviewed, for example, by P. J. Arpino and G. Guiochon in Analytical Chemistry, June 1979, vol. 51, p. 683A, and as discussed at the first workshop on liquid chromatography—mass spectrometry, held at Montreux in October 1981, the proceedings of which were published in Journal of Chromatography, 1982, volume 251 pps. 91–225. Amongst the many different approaches that have been used, two related techniques, known as electrohydrodynamic ionisation and electrospray ionisation, respectively, will be discussed here in greater detail because of their relevance to the present invention.

In the technique of electrohydrodynamic ionization, which is fully described by B. A. Stimpson and C. A. Evans Jnr. in Journal of Electrostatics, 1978, volume 5 p. 411, and Journal of Physical Chemistry, 1978, volume 82, p. 660, the solution is introduced into the vacuum system of the mass spectrometer through a capillary tube which is charged at high voltage relative to an extractor electrode situated immediately in front of it. This electrode is usually a thin disc with a hole in the centre, and the capillary tube is positioned concentric with the hole and so that its end is situated within the thickness of the disc. The solution to be analysed is ejected into the vacuum system through the capillary by means of a syringe, which is preferably motor driven. A high positive voltage (if positive ions are to be formed) is applied to the capillary, and the syringe plunger compressed to eject liquid into the vacuum system. If the correct conditions are employed (described below), electrohydrodynamic ionisation of the liquid will take place, and a beam of ions characteristic of the solute will be formed, which can be focussed into a conventional mass analyser. In general, it is necessary to use a solvent which has a low volatility (to ensure that the pressure in the vacuum system does not rise too high), and one which is strongly polar and has a reasonably high electrical conductivity. Glycerol with sodium iodide dissolved in it is frequently employed. These requirements are thought to be due to the fact that in electrohydrodynamic ionisation the electrical field does not actually ionise the solute molecules, but merely distorts the forces present at the surface of the liquid to such an extent that ions already present in the solution are directly emitted into the gas phase. These ions are then focussed into the mass spectrometer. Consequently it is necessary for the ions to be present in solution before it encounters the electrical field, and the process works best with with polar sample molecules dissolved in strongly polar solvents, or with a liquid metal sample. Another characteristic is that the flow rate of the solution is best kept at a very low level, so that no droplets of liquid emerge from the capillary. The sample ions are then emitted from sites round the tip of the capillary, and the shape of the capillary and its position relative to the extractor electrode have a profound effect on the efficiency of the ionization.

The electrohydrodynamic ionisation mass spectra of organic samples, obtained from glycerol and sodium iodide solvents, consist in general of peaks due to the molecular ion of the solute clustered with a variable number (between 0 and 10) of glycerol molecules and sometimes sodium ions, or in the case of negative ions, iodide ions. There is little fragmentation of the molecular ion, but the spectra are often difficult to interpret because of the formation of the complex clusters containing an unknown number of glycerol molecules. Further, the use of electrohydrodynamic ionisation sources with solvents other than glycerol and sodium iodide, although possible, is not always satisfactory because the degree of ionisation of the sample in the solution is usually lower, and more volatile solvents can give rise to problems of excessive pressure in the vacuum system due to evaporating solvent vapour. This problem can be reduced by using a nozzle skimmer system and an additional pumping stage in a similar way to that described below, but the ionisation process remains of low efficiency and for organic molecules the only really satisfactory results are obtained with glycerol solvents. Consequently the use of electrohydrodynamic ionisation for liquid chromatograpy—mass spectrometery is restricted.

In contrast with electrohydrodynamic mass spectrometery, electrospray mass spectrometery does not require glycerol and sodium iodide solvents. It is based on work by M. Dole et al, (described, for example, in Journal of Chemical Physics, 1968, volume 49, p. 2240). A solution containing the sample to be ionised is sprayed from a capillary tube into a region containing gas at approximately atmospheric pressure, towards a small orifice in a plate which leads into the vacuum system of the spectrometer. A high electrical potential is applied between the spraying capillary and the walls of the chamber containing the gas (including the plate with the small orifice). A separation device, usually a nozzle skimmer system like that described by Kantrowitz and Gray in the Review of Scientific Instruments, 1951, volume 22, p. 328, is placed between the region of atmospheric pressure and the vacuum system in order to reduce the quantity of gas flowing into the vacuum system, and to produce a better collimated molecular beam.

The principle of operation of the electrospray source is as follows. The sample to be ionised is dissolved in a solvent, preferably a fairly polar one, and the resultant solution is slowly displaced through the capillary into a region of high gas pressure and electrical field, as explained. As the jet of liquid emerges it becomes charged by the strong field, the solvent begins to evaporate and the jet breaks up into a series of small charged droplets. It was originally thought that these droplets would continue to evaporate until a point known as the Rayleigh limit was reached, where the drop would become unstable because of its increasing charge to volume ratio and break up into smaller drops, at least one of which would carry the charge. This process was thought to continue until all the solvent evaporated, leaving only neutral solvent molecules in the gas phase and ions of the solute, usually clustered with a few solvent molecules. However, the present inventors believe that it is unlikely that a droplet could evaporate sufficiently to reach the Rayleigh limit before an ion, usually solvated, would be lost from the charged drop by a process similar to electrohydrodynamic ionisation. Whatever the principle involved, it is clear from the original work of Dole that the electrospray technique produces ions from solutes of very high molecular weights (e.g. 500,000), and as the energy imparted to the ions is low, very little, if any, fragmentation of the ions takes place. It is therefore well suited for the ionisation of thermally unstable molecules, such as those frequently encountered in biochemistry.

Electrospray ionisation differs from electrohydrodynamic ionization chiefly in the fact that in the former the solution is sprayed into a gas at atmospheric pressure, whilst in the latter, liquid is pumped slowly through a capillary which leads into an evacuated region so that most of the solvent evaporates before it leaves the capillary and ionisation takes place largely at the tip of the capillary tube. Electrospray type ion sources have been interfaced with mass spectrometers, and the use of such a combination for liquid chromatography—mass spectrometry is known. A typical system is described in U.S. Pat. No. 4,209,696.

A process which is related to electrospray ionisation has been developed by J. V. Iribarne and B. A. Thompson, and is described in U.S. Pat. No. 4,300,044. In this process, a solution containing the sample to be ionised is sprayed from a capillary into gas at atmospheric pressure, and the resultant jet of liquid is nebulized by means of a jet of compressed air flowing at right angles to the liquid jet. The droplets of liquid formed in this way are then electrically charged by induction from a high voltage electrode placed close to the nebulizing jet of air. This process is carried out in the mouth of a wide bore tube, into which the charged droplets are swept. The gas flow containing the drops is then directed across the surface of a plate containing a small hole which leads into the mass spectrometer analyser, and the ions formed as the droplets evaporate are caused to enter this hole by means of an electric field applied at right angles to the gas flow. A curtain of inert gas (e.g. carbon dioxide) flows between the plate which contains the hole and a second plate situated a short distance behind it. This is at a higher pressure than the gas in the remainder of the source and consequently escapes through the orifice in the first plate into the source region. This curtain gas serves to isolate the mass spectrometer vacuum system from excessive flows of solvent vapour, water vapour and other contaminants, and enables cryopumping to be carried out in the vacuum chamber of the mass spectrometer by ensuring that most of the gas that enters the vacuum chamber is the cryopumpable curtain gas. However, the process described is not a true electrospray source because the droplets are produced by a jet of air and are charged by induction, whereas in the true electrospray source they are produced by the action of an electric field on the jet of liquid, and no additional nebulization or charging is required.

The main disadvantage encountered with the prior art electrospray ionization systems, such as that described, is that, like electrohydrodynamic ionisation, the ions produced are usually clustered with a variable number of solvent molecules, although this number tends to be smaller than in electrohydrodyamic ionisation. It is thought that the clustering arises from the fact that during the last stages of evaporation the droplets are virtually stopped by collisions with the inert gas molecules, and the remaining collisions due to thermal motion of the gas molecules are not usually sufficiently energetic to remove the last remaining solvent molecules clustered round the sample ion. In U.S. Pat. No. 4,209,696, additional desolvation is achieved by accelerating the solvated ions after they emerge into the vacuum system in a region close to the orifice where the gas pressure is still fairly high. The increased energy of the collisions of the gas molecules is then sufficient to remove more of the solvent molecules from the ions. The ions are then decelerated again in a region further from the orifice where the pressure is lower and there is a much smaller probability of reassociation between the solvent molecules and the ions. A very similar process is described in U.S. Pat. No. 4,121,099, which also describes another problem encountered with prior art electrospray ion sources, that is the problem of providing an efficient focussing action which does not impart a significant energy spread to the ions and which would degrade the performance of the mass spectrometer. The patent suggests a possible solution to the problem by the provision of strong focussing fields in a region very close to the orifice in the free jet expansion where the pressure is high enough for collisions between the gas molecules and the ions to limit the amount of energy that can be imparted to the ions, thereby limiting the energy spread that is imparted to the ions during the focussing process. Additional lens elements may also be provided further from the nozzle to achieve the declustering effect discussed above. However, it is not possible to completely separate the focussing and declustering actions, and it is difficult to optimise both features simultaneously.

When a magnetic sector spectrometer is to be used, the potential of the inlet capillary of the electrospray source must in general be maintained at a value at least as great as the accelerating voltage required by the spectrometer, and the focussing problem is worsened because the ions still emerge through the orifice into the low pressure region with a very low kinetic energy. They must therefore be reaccelerated to the energy required by the spectrometer. It is difficult to construct electrostatic lenses which will achieve this without significant loss of transmission efficiency and broadening of the kinetic energy spectrum of the ions, and when the design of the acceleration step is further constrained by the desolvation requirements it becomes even more difficult. There is considerable advantage, therefore, in completely separating the desolvation stage from the focussing stage so that both processes can be optimised independently, and so that the need to accelerate the ions to cause desolvation can be eliminated. It is an object of the present invention, therefore, to provide means for desolvating the ions and effectively controlling the extent of the desolvation, before they leave the region of the source which is maintained substantially at atmospheric pressure.

SUMMARY OF THE INVENTION

In accordance with one aspect of this invention there is provided a method of generating ions for mass spectral analysis from a sample dissolved in a solution by electrospray ionization the improvement comprising:

(a) causing said solution to flow through a capillary tube or jet;

(b) maintaining a high electrical potential difference between said capillary tube or jet and a first conductive wall spaced from and disposed facing the outlet of said capillary tube or jet thereby causing said solution to be electrosprayed from said outlet;

(c) maintaining the ambient pressure between said outlet and said wall at substantially atmospheric pressure;

(d) providing between said wall and said outlet a flow of inert gas substantially counter to the flow from said outlet;

(e) providing an orifice in said wall in alignment with the axis of said capillary tube or jet at the outlet thereof; and (f) maintaining the pressure on the side of said wall remote from said outlet at a reduced pressure whereby gas containing ions from said solution characteristic of said sample flows through said orifice.

In a preferred aspect of the method of the invention, the gas and ions flowing through said orifice away from said outlet are subsequently subjected to one or more additional pressure reduction, focussing on ion accelerating operations prior to the mass spectral analysis of the ion beam so generated.

In accordance with a further aspect of this invention there is provided an apparatus for generating ions for mass spectral analysis from a sample dissolved in a solution by means of electrospray ionisation, comprising:

(a) a capillary tube or jet through which the said solution may be caused to flow leading into a first chamber having a first conductive wall spaced from and disposed facing the outlet of the said capillary, means for maintaining a high electrical potential difference between said outlet and said first conductive wall whereby said solution may be electrosprayed from said outlet into said first chamber;

(b) and an inlet pipe or pipes through which an inert gas may be introduced into said first chamber between said wall and said outlet in a direction substantially counter to the flow from said outlet, and an outlet pipe or pipes leading from said first chamber to a region at substantially atmospheric pressure whereby the ambient pressure in said first chamber may be maintained at substantially atmospheric pressure or a slightly greater pressure; and (c) an orifice in said first conductive wall and aligned with the axis of said capillary tube or jet at the outlet thereof and leading into a second chamber which is provided with means for maintaining therein a reduced pressure whereby a flow of ions from said solution characteristic of said sample into said second chamber may be maintained.

Preferably the apparatus additionally comprises one or more means for further preparing the ion beam emerging through said orifice into said second chamber for mass analysis said means for further preparing being selected from additional pressure reduction means, focussing means and ion accelerating means.

In accordance with a further aspect of the invention there is also provided a mass spectrometer containing ion beam generating means comprising an apparatus according to the invention.

Thus, in the present invention, the desolvation of the ions formed in the electrospray process takes place in the first chamber by virtue of the flow of gas maintained in that chamber. The solvated ions produced in the electrospray $(M^+)S_x$ exist in a dynamic equilibrium with the solvent molecules S and the desolvated ions $M^+$, that is:

$$(M^+)S_x \rightleftarrows M^+ + xS$$

and this equilibrium is displaced to the right by removing the solvent molecules S. This is achieved by means of a flowing inert gas, in contrast with prior art electrospray systems (e.g. U.S. Pat. No. 4,209,696) in which the gas is essentially static and consists largely of the solvent vapour. The presence of solvent molecules in the vapour phase clearly displaces the equilibrium to favour the production of the solvated species $(M^+)S_x$. The inert gas employed may be any gas which does not chemically react with the solvent or the expected samples, for example any of the noble gases, e.g., helium, neon, argon, or nitrogen or carbon dioxide. Nitrogen is generally used because it is relatively cheap, but other gases may be used if desired. Preferably the gas should be pure in order to prevent the formation of ions in the electrospray from impurities introduced in the gas, and to prevent the deposition of water and other condensable impurities in the electrospray chamber. The degree of desolvation of the ions can be varied by adjusting the flow of inert gas in the chamber. Substantially complete desolvation can be achieved in most cases with a flow of approximately 200 at.cc.$s^{-1}$, but the flow rate required is dependent on the nature and the flow rate of the solution and the dimensions of the electrospray chamber. Typically the flow rate will be between 50 and 500 at.cc.$s^{-1}$ of nitrogen.

The gas should be introduced into the electrospray chamber in a direction opposite to that of the flow from the capillary to ensure the most efficient desolvation of the ions. This can be done by introducing it close to the wall of the electrospray chamber which contains the exit orifice by means of a pipe or pipes which are positioned so that the flow is in the required direction, or by a series of pipes that pass through the wall itself. Alternatively, a perforated diaphragm, containing a number of small holes and a larger hole at its centre to allow the passage of the electrospray jet, may be positioned between the outlet of the capillary and the wall of the chamber, suitably approximately half way between the outlet and the wall, and the gas introduced between the diaphragm and the wall. The gas will then flow in the required direction through the remainder of the chamber from the perforations in the diaphragm. Preferably the outlet pipe of the chamber should be positioned in the end wall of the chamber through which the capillary passes, and should be substantially larger than the inlet pipes or pipes. In general, the outlet pipe should vent at atmospheric pressure so that the electrospray chamber remains substantially at, or slightly greater than, atmospheric pressure.

In many cases, the efficiency of the desolvation process is improved, and the maximum permissible solution flow rate increased, if the inert gas is heated prior to its introduction into the electrospray chamber. The additional heat input to the evaporating drops in the electrospray produced by the use of a heated gas helps to prevent their temperature falling as they evaporate due to the latent heat of vaporisation and consequently improves the efficiency of the solvent removal and increases the maximum solution flow rate which can be used. Any suitable means can be used to heat the gas prior to its introduction. Preferably the temperature of the gas should be between 25° and 100° C., and good results are usually obtained at about 60° C. The temperature should however be adjusted along with the flow rate of inert gas to obtain the desired degree of desolvation for a given solution and solution flow rate.

Although electrospraying of the solution can be effected simply by maintaining a potential difference between the inlet capillary and the opposite wall of the chamber, the process is more controllable if additional electrodes are placed in the electrospray chamber to focus the spray of charged droplets. These electrodes may conveniently take the form of a number (typically two or three) of cylindrical electrodes arranged between the capillary outlet and the first conductive wall and about the axis of the capillary and which form the walls of the electrospray chamber. The potentials applied to these electrodes should preferably be adjusted to maximise the generation of ions oy the electrospray source, and will lie between the capillary and wall potentials.

The electrospray source may be used to generate either positive or negative ions from the dissolved sample. Positive ions are formed if the capillary and focussing electrodes are positive with respect to the end wall, and negative ions are formed if they are negative.

It will be appreciated that a stable electrospray is only obtained for a particular solution under certain conditions of liquid flow rate and electrical potentials. Another feature of the invention is that it has been found that heating the inlet capillary stabilizes the spray in conditions where it would not otherwise be possible to produce a stable electrospray. Heating the inlet capillary therefore allows the use of a wider range of flow rates and potentials in the electrospray chamber, which allows better optimisation of the efficiency of the process and sometimes permits electrospray ionisation to be achieved with a particular solution at flow rates that would otherwise be impossible. Heating the capillary also increases the total ion currents generated by the source when a small bore capillary is used.

It has also been found that the introduction of oxygen in the region of the outlet of the inlet capillary sometimes supresses arcing in the electrospray chamber which occurs under certain conditions, especially when negative ions are being generated. Both these features of the invention will be described later.

Preferably the orifice in the end wall of the electrospray chamber should be formed as a small hole in the centre of a hollow conical frustum which forms part of the end wall and is orientated with its small diameter end facing the inlet capillary. The frustum serves as a skimmer and its use increases the total ion current generated by the source in comparison with that obtained with a planar orifice. The orifice itself should be as large as possible subject to the requirement of maintaining a sufficiently low pressure in the second chamber, and its diameter is therefore dependent on the speed of the vacuum pump used to evacuate the second chamber. Typically the pressure in this chamber should not exceed $10^{-3}$ torr.

In general, the potentials applied to the electrospray system will be such that the inlet capillary is at a high positive voltage (for positive ion production), and the ions will emerge with a low kinetic energy, e.g. 25 eV, as described in U.S. Pat. No. 4,209,696. The kinetic energy of the ions is then at a value suitable for their direct introduction into a quadrupole mass spectrometer, which might be positioned in the second evacuated chamber. However, it is more likely that the pressure in this chamber will be too high for the proper operation of the spectrometer, especially if the efficiency of the electrospray ionisation is to be maintained, and it is then desirable to place the spectrometer in a third region of still lower pressure, and use a second nozzle-skimmer arrangement to transmit the ions into the third region. Such arrangements are well known, and are described in U.S. Pat. No. 4,209,696. Additional electrostatic lenses can also be provided in the second and third chambers to optimise the transmission of ions into the mass spectrometer.

When a magnetic sector mass spectrometer is to be used, the inlet capillary of the electrospray source must in general be maintained at a potential at least as high as the accelerating voltage required by the spectrometer in order that they will have sufficient potential energy to permit them to be reaccelerated to the required energy after they emerge into the second chamber with low kinetic energy. The reacceleration can be achieved by provision of a suitable electrostatic lens system in the second chamber, preferably situated close to the orifice, as described in U.S. Pat. No. 4,121,099, but a better method is to use the invention disclosed in our copending U.S. patent application Ser. No. 486,642 entitled "Process and Apparatus for Changing the Energy of Charged Species Entrained in a Flowing Gaseous Medium." This application also discloses means by which the inlet capillary may be operated at ground potential, even when a magnetic sector mass spectrometer is used, and the use of this invention greatly simplifies the construction of efficient lens systems for adjusting the energy of the ions formed in the electrospray to the value required by the mass spectrometer.

BRIEF DESCRIPTION OF THE DRAWINGS

The invention will be described in greater detail by reference to the drawings, in which.

DETAILED DESCRIPTION OF THE INVENTION

Figure 1:
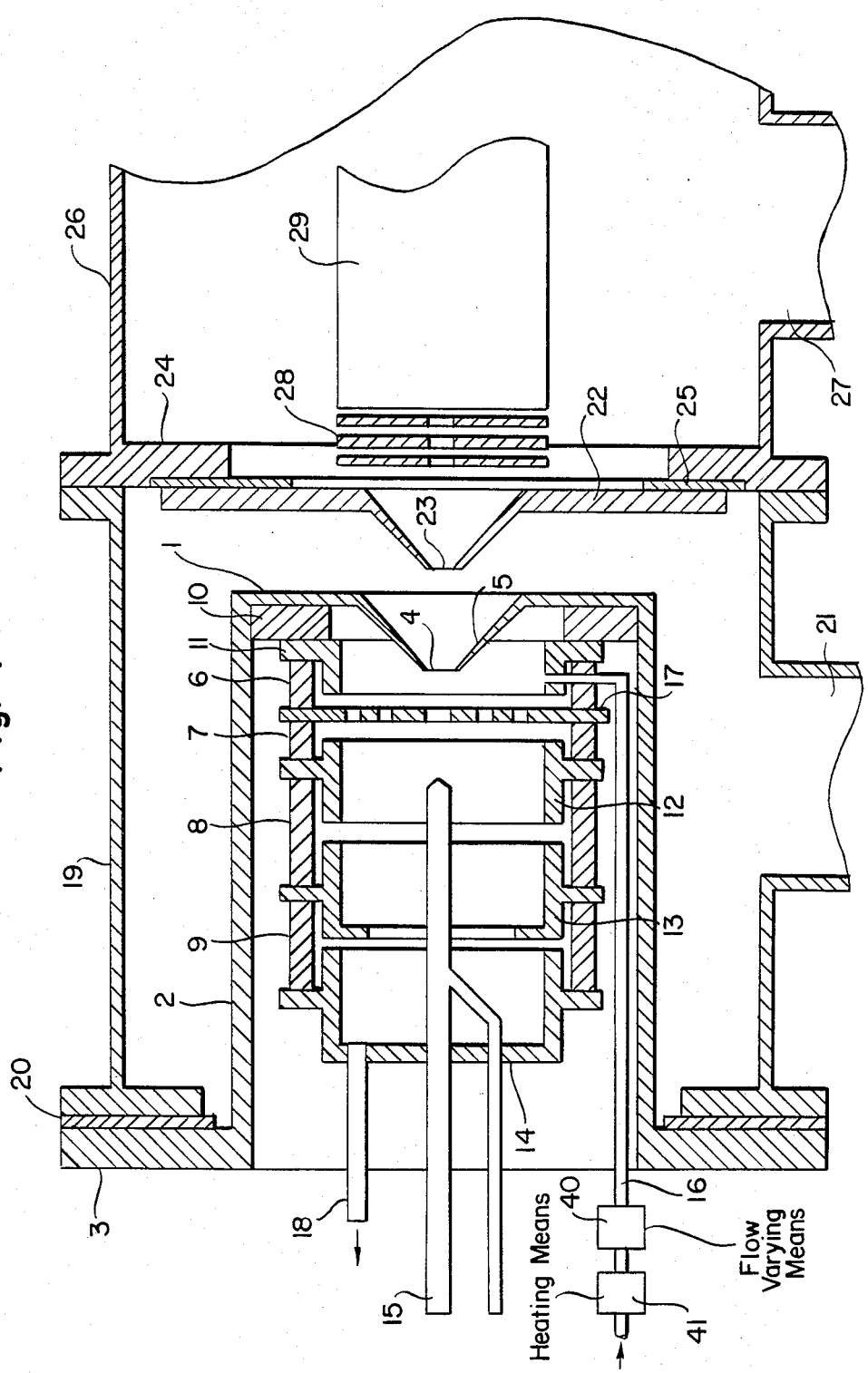
FIG. 1 is a simplified sectional view of an electrospray ion source constructed according to the invention.

Referring first to FIG. 1, the electrospray source itself is mounted on end plate 1 which is supported at the end of tube 2 from flange 3. End plate 1 is also the first conductive wall of the electrospray chamber and contains a small orifice 4 in a conical frustum which also serves as a skimmer 5. The gas tight electrospray chamber itself is formed by four cylinders 6,7,8 and 9, and four externally flanged cylindrical electrodes 11,12, 13 and 14, which largely form its inner surface, all of which are attached to the end plate 1 by means of insulator 10. The cylinders 6-9 are made from an electrically insulating material such as PTFE, so that the conductive electrodes 11-14 are insulated from each other. Alternatively, the electrodes may be fastened together with insulating washers and securing means to obviate the need for the cylinders 6-9. The electrospray capillary 15 is fitted into the end electrode 14 by means of a gas tight union. "O" ring seals are incorporated between the various parts which comprise the electrospray chamber to ensure that it is gas tight.

Figure 4:
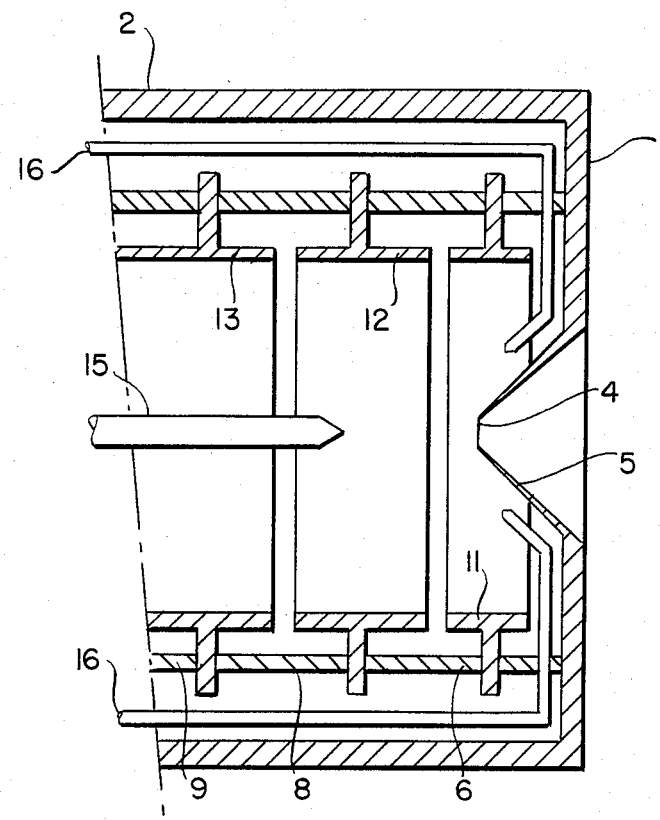
Figure 5:
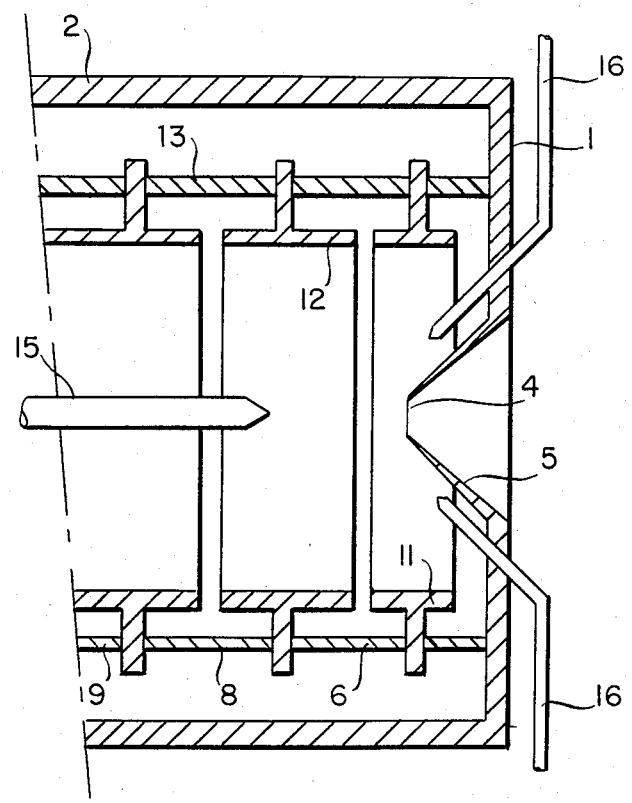

In the embodiment shown in FIG. 1, a flow of inert gas is introduced into pipe 16 and emerges in the front section of the chamber between the skimmer 5 and a perforated diaphragm 17, which is supported between cylinders 6 and 7. The inert gas flow is directed by the outer surface of the skimmer 5 and the holes in plate 17 to flow through the electrospray chamber in the opposite direction to the flow emerging from capillary 15 to leave via tube 18 which vents at atmospheric pressure, so that the pressure in the electrospray chamber is maintained at, or slightly above, atmospheric pressure. Alternatively, diaphragm 17 may be omitted and inlet pipes 16 may be positioned as shown in FIGS. 4 and 5 to produce an inert gas flow substantially counter to the flow from capillary 15. Conveniently, the flow of inert gas is controlled using flow varying means 40 to control the degree of desolvation of the ions electrosprayed from capillary 15. The source may also be provided with heating means 41 for heating the inert gas before it enters the electrospray chamber.

Flange 3, which supports the electrospray chamber, is attached to vacuum housing 19 by means of insulator 20, and a vacuum pump is attached to port 21. This pump is typically a diffusion pump with a speed of aproximately 1000 l. s$^{-1}$, but any pump capable of maintaining the pressure in housing 19 at less than 10$^{-3}$ torr in the presence of the gas flow through orifice 4 can be used. Flange 3 is insulated from housing 19 in order that a variable electrical potential can be applied to the end plate 1 and skimmer 5 when housing 19 is at earth potential.

A second conical skimmer 22 containing an orifice 23 is positioned on the end wall of the housing 19 on a flange 24 which forms part of the second vacuum housing 26. The plate carrying the skimmer 22 is insulated from flange 24 by insulator 25, and all the joints between the flanges are made in a vacuum tight manner. Housing 26 is pumped by any suitable high vacuum pump such as a diffusion pump or a turbomolecular pump through port 27, so that a pressure of better than 10$^{-4}$ torr, or preferably 10$^{-5}$ torr, is maintained in housing 26. A series of electrostatic lens elements 28 serves to focus the ion beam emerging through orifice 23 into mass spectrometer 29, which in this case is a conventional quadrupole mass filter.

In the description given above, and in FIG. 1, many of the details concerning the construction of the vacuum seals and flanges, and the means used to fasten them together, incorporating electrical insulation where necessary, have been omitted. Such details are standard features of vacuum systems and are well known.

Figure 2:
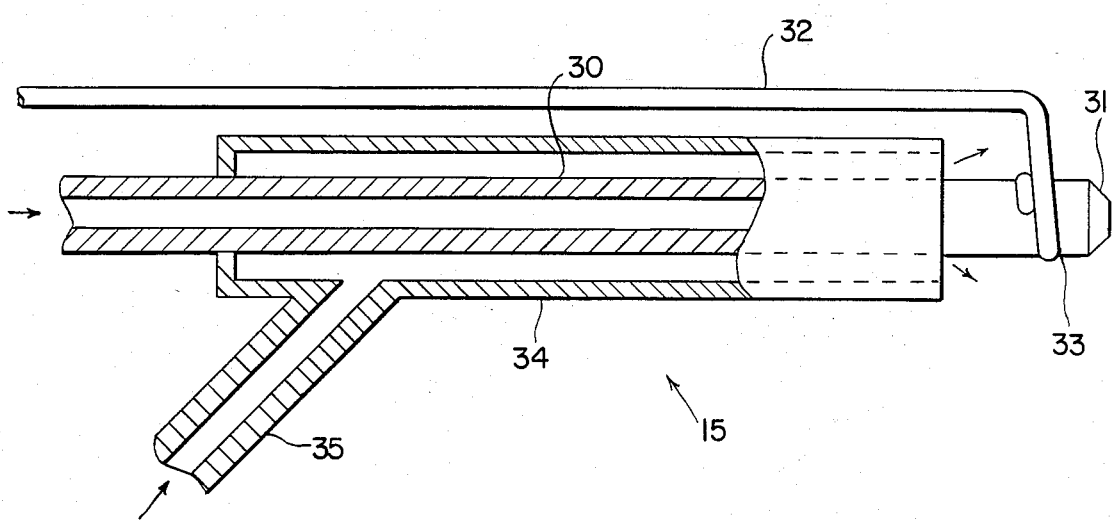
FIG. 2 is a detailed view of an electrospray inlet capillary suitable for use with the source shown in FIG. 1.

The electrospray capillary assembly 15 is illustrated in greater detail in FIG. 2. The needle 30 should be a good electrical conductor and be chemically inert, and is preferably made from stainless steel. Optimum performance is obtained when the tip 31 is ground into a sharp cone with steep sides. The inside diameter is preferably within the range 0.025 mm to 0.100 mm, and the outside diameter should be large enough to ensure mechanical rigidity. Hypodermic syringe needles can frequently be used for needle 30. The end of the needle may be heated by passing an electrical current through it by means of wire 32, which is silver soldered to the needle close to the tip at point 33. It has been found that heating the capillary can improve the stability of the electrospray, as explained above. It has also been found that the addition of oxygen close to the tip of the capillary can reduce the tendency for arcing in the electrospray chamber to occur, which is particularly troublesome in the negative ion mode. The oxygen can conveniently be supplied by enclosing the needle 30 in a larger bore open ended tube 34 and supplying oxygen through a side arm 35. Neither the heating or the addition of oxygen are essential, however, and both these features can be omitted if desired.

The capillary assembly 15 is secured by a union in the end electrode 14 of the electrospray chamber, and is maintained at a high potential relative to the end plate 1 of the chamber. The end plate 1 is supported on tube 2 from flange 3 which is insulated from the housing 19 so that it can be used as an electrostaic focussing element with a relatively low potential applied to it. Electrodes 11, 12 and 13 complete the inside surface of the electrospray chamber, as explained, and different variable potentials may be applied to the electrodes to optimise the electrospray process. The gap between the electrodes should be kept as small as possible in order to ensure that the walls of the chamber are electrically conducting over the maximum possible area so that the build up of electrical charge on insulated sections of the wall, which might otherwise destabilise the electrospray, is minimized.

As required by the invention, the optionally heated inert gas is introduced through pipe 16 into the space between end plate 1 and a perforated diaphragm 17, which also serves as a focussing electrode. Diaphragm 17 serves to direct the gas flow counter to the flow from the capillary outlet, and has a larger hole at its centre through which the electrospray jet passes. It is positioned midway between the end of capillary 15 and end plate 1. The surfaces and edges of all the electrodes in the electrospray chamber should be well polished to minimise the possibility of sparking. It will be appreciated that it is not essential to split the wall of the electrospray chamber in as many places as described, and in many cases satisfactory performance can be obtained with fewer electrodes. For example, electrodes 12 and 13 could be connected together, or made in one piece, as could electrode 11 and plate 17.

In order to produce positive ions, capillary 15 is maintained at a high positive potential relative to end plate 1, and the other electrodes at appropriate intermediate potentials, adjusted to optimise performance. Negative ions can be produced by changing the polarity of all the electrodes.

It has been found that there are two modes of electrospraying, dependent on the potential difference between the capillary and the end plate. If this is between 3 and 6 KV, the "low voltage" mode is observed, and the ionisation of the sample is very gentle resulting in very little, if any, fragmentation of the sample. If the potential difference is greater than 6 KV, a corona discharge is formed in the chamber, and the ionisation is more energetic, resulting in some fragmentation of the sample ions. Usually the source is operated at the upper end of the "low voltage" mode in order to achieve maximum sensitivity with minimum fragmentation. The electrospray is only stable given certain geometrical arrangements and potentials. The best results are generally obtained with the capillary 1.5 cm from orifice 4 in skimmer 5, but the optimum distance is dependent on the potentials, and the flow rate and composition of the solution, as well as the flow of inert gas. It is an advantage to make this distance variable. In all cases the diameter of the electrospray chamber should be at least twice the capillary to end plate distance, and preferably larger, but if the chamber is too large, the quantity of inert gas required becomes too great.

The voltages applied to the focussing electrodes are adjusted to optimum ion generation in the electrospray and to ensure a stable spray. Typical conditions for the generation of positive ions are:

$V_{14}, V_{15} = +6$ KV, $V_{12}, V_{13} = +1.5$ KV, $V_{17}, V_{11} = +1.0$ KV, $V_1, V_5 = +100$ V, where the subscript numbers refer to the electrodes identified by those numbers in FIG. 1, and the voltages are all relative to the housing 19 which is at earth potential.

Figure 3:
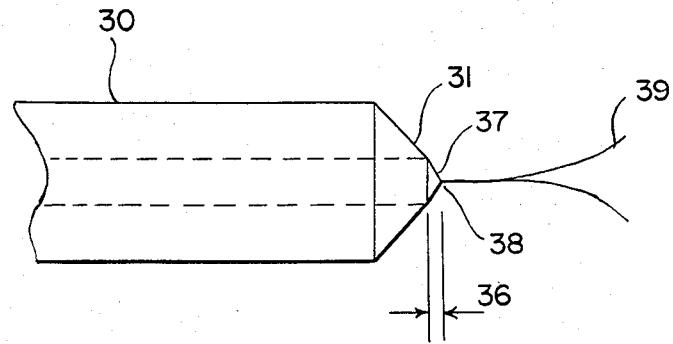
FIG. 3 is a drawing of the liquid jet as it leaves the tip of the inlet capillary under electrospray conditions and FIGS. 4 and 5 are sectional views of part of an electrospray ion source constructed according to the invention showing alternative means for introducing the inert gas.

The conditions over which stable electrospraying can be achieved can be extended by heating the capillary by passing an electrical current through it, as described. FIG. 3 is a drawing of the electrospray jet as it leaves the tip 31 of the needle 30. It consists of a small cone of liquid 37 which extends through the distance 36 to point 38. The true electrospray jet 39 starts at point 36, as shown. It is thought that heating the capillary reduces distance 36, which results in the formation of stable jets over a wider range of capillary internal diameters and flow rates, etc. It also results in greater ion currents when very small bore capillaries are used, and improves the overall efficiency of the process. However, it is possible that some thermal degradation of sensitive samples might be caused by heating the capillary.

There are some limitations on the flow rate and composition of the solution if successful electrospraying is to be obtained. Flow rates between 1 and 100 microliters per minute can be used, but in general the best results are obtained at the lowest flow rate. The solvent should be such that there is either electron or proton affininty with the expected samples, and it should be polar and preferably contain an ionic solute in addition to the sample. These requirements mean that when used as a liquid chromatograph—mass spectrometer interface, the electrospray source works well with highly polar solvents such as water or methanol, especially when the solvent contains additional dissolved salts such as buffers, in contrast with most other forms of LC-MS interfaces.

The inert gas introduced into the source should preferably consist of a fairly pure gas such as nitrogen, helium, or argon, etc. As explained, the degree of desolvation of the ions can be varied by adjusting the flow rate of the gas and its temperature. The flow rate required for a particular degree of desolvation is of course dependent on the liquid flow, and typically a flow of 200 at.cc.s$^{-1}$ is used for a liquid flow rate of 10 microliters per minute, at a temperature of 60° C. to ensure complete desolvation. Flow rates from 50 to 500 at.cc.s$^{-1}$ and temperatures from 25° C. to 100° C. can be used, however.

The ions generated in the electrospray process pass through orifice 4 in skimmer 5 into an evacuated region in housing 19 where the pressure is maintained at $10^{-3}$ torr or less by a vacuum pump connected to port 21.

The electrical potential applied to end plate 1 is adjusted to obtain optimum transmission of the ions. Additional electrostatic lens elements can be provided behind orifice 4 for additional focussing of the ion beam if desired. Alternatively, means can be provided in this region to accelerate the ions to another kinetic energy, as described previously.

The focussed ion beam then passes through an orifice in a second skimmer 23 into a region of still higher vacuum which contains the mass spectrometer 29. Unless means are provided for reaccelerating the ions, this must be a mass filter capable of accepting ions with very low energies, such as a quadrupole analyser. The potential on plate 22 which supports the skimmer is also made variable to assist in focussing the ion beam, and more electrostatic lenses 28 are provided to ensure maximum efficiency of transmission of ions into the spectrometer. Typically, for a quadrupole analyser, plate 22 and the first element of lens 28 will be maintained at about $+25$ V, for the conditions given previously. This potential determines the energy with which the ions enter the spectrometer. The second skimmer is provided to allow a higher vacuum to be maintained in the region of the mass spectrometer whilst maintaining an efficient transfer of ions, and devices of this type are well known.

It will be appreciated that the source described above is intended by way of example only, and that it is possible to construct an electrospray source incorporating the invention in a variety of alternative ways, which will be apparent to those skilled in the art.

What is claimed is:

1. In a method of generating ions for mass spectral analysis from a sample dissolved in a solution by electrospray ionization the improvement comprising:
   (a) causing said solution to flow through a capillary tube or jet;
   (b) maintaining a high electrical potential difference between said capillary tube or jet and a first conductive wall spaced from and disposed facing the outlet of said capillary tube or jet thereby causing said solution to be electrosprayed from said outlet;
   (c) maintaining the ambient pressure between said outlet and said wall at substantially atmospheric pressure;
   (d) providing between said wall and said outlet a flow of inert gas substantially counter to the flow from said outlet;
   (e) providing an orifice in said wall in alignment with the axis of said capillary tube or jet at the outlet thereof; and
   (f) maintaining the pressure on the side of said wall remote from said outlet at a reduced pressure whereby gas containing ions from said solution characteristic of said sample flows through said orifice.

2. A method according to claim 1 wherein gas and ions flowing through said orifice away from said outlet are subsequently subjected to one or more additional pressure reduction, focussing or ion accelerating operations prior to the mass spectral analysis of the ion beam so generated.

3. A method according to claim 1 in which the flow rate of the inert gas is varied to control the degree of desolvation of the ions formed by the electrospray process.

4. A method according to claim 3 in which the flow rate of the inert gas lies within the range 50–500 at.cc.s$^{-1}$.

5. A method according to claim 4 in which the flow rate of the inert gas is about 200 at.cc.s$^{-1}$.

6. A method according to claim 1 in which the inert gas is selected from the group consisting of helium, neon, argon, carbon dioxide and nitrogen.

7. A method according to claim 1 in which said inert gas is introduced through an inlet pipe or pipes situated close to said first conductive wall, said inlet pipe or pipes being angled so that the flow of inert gas is substantially counter to the flow from said outlet.

8. A method according to claim 1 in which said inert gas is introduced through an inlet pipe or pipes which pass through said first conductive wall in a direction such that the flow of inert gas is substantially counter to the flow from said outlet.

9. A method according to claim 1 in which a perforated diaphragm containing a plurality of small holes and a substantially larger hole at its centre is placed between the outlet of said capillary and said first conductive wall, and said inert gas is introduced into the space between said diaphragm and said wall.

10. A method according to claim 9 in which said perforated diaphragm is maintained at an electrical potential selected to maximise the generation of ions in the electrospray process.

11. A method according to claim 1 in which the inert gas is heated before its admission between said wall and said outlet.

12. A method according to claim 11 in which the temperature of said inert gas is maintained between 25° and 100° C.

13. A method according to claim 11 in which the temperature of said inert gas is maintained at about 60° C.

14. A method according to claim 11 in which the temperature of said inert gas is adjusted to obtain a desired degree of desolvation of the ions formed in the electrospray process.

15. A method according to claim 1 in which said capillary tube or jet passes through an end electrode disposed opposite to said first conductive wall, and wherein a plurality of substantially cylindrical electrodes are arranged along the axis of the said capillary tube or jet between said first conductive wall and said end electrode, said cylindrical electrical being maintained at electrical potentials selected to maximise the generation of ions in the electrospray process.

16. A method according to claim 1 in which oxygen is introduced close to the outlet of said capillary tube or jet in addition to said inert gas.

17. A method according to claim 1 in which said capillary tube or jet is heated.

18. A method according to claim 17 in which said capillary tube or jet is heated by passage of an electrical current therethrough.

19. A method according to claim 1 in which said first conductive wall is provided with a hollow conical frustum the apex of which is directed towards said outlet and which defines said orifice in said first conductive wall.

20. Apparatus for generating ions for mass spectral analysis from a sample dissolved in a solution by means of electrospray ionisation, comprising:

(a) a capillary tube or jet through which the said solution may be caused to flow leading into a first chamber having a first conductive wall spaced from and disposed facing the outlet of the said capillary, means for maintaining a high electrical potential difference between said outlet and said first conductive wall whereby said solution may be electrosprayed from said outlet into said first chamber;

(b) and an inlet pipe or pipes through which an inert gas may be introduced into said first chamber between said wall and said outlet in a direction substantially counter to the flow from said outlet, and an outlet pipe or pipes leading from said first chamber to a region at substantially atmospheric pressure whereby the ambient pressure in said first chamber may be maintained at substantially atmospheric pressure or a slightly greater pressure; and (c) an orifice in said first conductive wall and aligned with the axis of said capillary tube or jet at the outlet thereof and leading into a second chamber which is provided with means for maintaining therein a reduced pressure whereby a flow of ions from said solution characteristic of said sample into said second chamber may be maintained.

21. Apparatus according to claim 20 further comprising one or more means for further preparing the ion beam emerging through said orifice into said second chamber for mass analysis said means for further preparing being selected from additional pressure reduction means, focussing means and ion accelerating means.

22. Apparatus in accordance with claim 20 incorporating means for the varying the flow of said inert gas in order to vary the degree of desolvation of the ions electrosprayed from said outlet of said capillary tube or jet.

23. Apparatus according to claim 22 in which said means for varying the flow are capable of maintaining said flow of said inert gas at between 50 and 500 at.cc.s$^{-1}$.

24. Apparatus according to claim 23 in which said means for varying the flow are capable of maintaining said flow of said inert gas at about 200 at.cc.s$^{-1}$.

25. Apparatus according to claim 20 in which said inlet pipe or pipes comprises at least one pipe which enters said first chamber close to said first conductive wall, said pipe or pipes being angled so that the flow of inert gas is substantially counter to the flow from said capillary tube or jet.

26. Apparatus according to claim 20 in which said inlet pipe or pipes comprises at least one pipe which passes through said first conductive wall in a direction such that the flow of inert gas is substantially counter to the flow from said outlet.

27. Apparatus according to claim 20 further comprising a perforated diaphragm containing a plurality of small holes and a substantially larger hole at its centre, situated in said first chamber between the outlet of said capillary tube or jet and said first conductive wall, said inlet pipe or pipes opening into said first chamber between said diaphragm and said first conductive wall.

28. Apparatus according to claim 27 in which said perforated diaphragm is provided with means to maintain it at an electrical potential selected to maximise the generation of ions by the electrospray process.

29. Apparatus according to claim 20 further comprising means for heating the inert gas before its admission into said first chamber.

30. Apparatus according to claim 29 further comprising means for maintaining the temperature of said inert gas between 25° and 100° C.

31. Apparatus according to claim 29 further comprising means for maintaining the temperature of the inert gas at about 60° C.

32. Apparatus according to claim 29 further comprising means for adjusting the temperature of said inert gas to vary the degree of desolvation of the ions electrosprayed from said outlet.

33. Apparatus according to claim 20 in which said first chamber incorporates an end electrode through which said capillary tube or jet passes, and in which a plurality of substantially cylindrical electrodes are arranged in said first chamber along the axis of said capillary tube or jet between said first conductive wall and said end electrode, said cylindrical electrodes being provided with means by which they may be maintained at electrical potentials selected to maximize the generation of ions in the electrospray process.

34. Apparatus according to claim 20 further comprising an additional inlet pipe adapted to introduce oxygen close to the outlet of said capillary tube or jet.

35. Apparatus according to claim 20 in which said capillary tube or jet is provided with a source of electrical current whereby said capillary tube or jet may be heated by the passage of the electrical current therethrough.

36. Apparatus according to claim 20 in which said first conductive wall is provided with a hollow conical frustum the apex of which is directed towards said outlet and which defines said orifice in said first conductive wall.

37. A mass spectrometer containing ion beam generating means comprising an apparatus as claimed in claim 20.

* * * * *

UNITED STATES PATENT AND TRADEMARK OFFICE
CERTIFICATE OF CORRECTION

PATENT NO. : 4,531,056
DATED : July 23, 1985
INVENTOR(S) : Michael J. LABOWSKY et al It is certified that error appears in the above-identified patent and that said Letters Patent is hereby corrected as shown below:

In column 1, on line 6, under the Title add the following:

--This invention was made with Government support under grants ET-78-G-01-34261 awarded by the Department of Energy, and ENG-7910843 awarded by the National Science Foundation. The Government has certain rights in this invention--.

Signed and Sealed this

Eighteenth Day of March 1986

[SEAL]

Attest:

DONALD J. QUIGG

Attesting Officer

Commissioner of Patents and Trademarks